US010025271B2

(12) United States Patent
Mathuis et al.

(10) Patent No.: US 10,025,271 B2
(45) Date of Patent: *Jul. 17, 2018

(54) METHOD AND SYSTEM FOR DETECTING AND/OR CLASSIFYING CANCEROUS CELLS IN A CELL SAMPLE

(71) Applicant: Ovizio Imaging Systems NV/SA, Brussels (BE)

(72) Inventors: Philip Mathuis, Brussels (BE); Serge Jooris, Brussels (BE); Olivier Magniette, Deurle (BE)

(73) Assignee: Ovizio Imaging Systems NV/SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,796

(22) Filed: Apr. 26, 2017

(65) Prior Publication Data

US 2017/0261930 A1  Sep. 14, 2017

Related U.S. Application Data

(63) Continuation of application No. 14/233,562, filed as application No. PCT/EP2012/063936 on Jul. 16, 2012, now Pat. No. 9,684,281.

(30) Foreign Application Priority Data

Jul. 19, 2011 (EP) .................................... 11174583
Nov. 21, 2011 (EP) .................. PCT/EP2011/070571

(51) Int. Cl.
*G06K 9/00* (2006.01)
*G03H 1/04* (2006.01)
(Continued)

(52) U.S. Cl.
CPC ....... *G03H 1/0443* (2013.01); *G01N 15/1434* (2013.01); *G01N 15/1475* (2013.01);
(Continued)

(58) Field of Classification Search
CPC ............... G03H 1/0443; G03H 1/0005; G03H 2001/005; G01N 15/1434; G01N 15/1475;
(Continued)

(56) References Cited

U.S. PATENT DOCUMENTS 4,786,594 A   11/1988  Khanna et al.
5,089,416 A    2/1992  Schwartz
(Continued)

FOREIGN PATENT DOCUMENTS

CN   202 808 799        3/2013
EP      0479231 A1      4/1992
(Continued)

OTHER PUBLICATIONS

Kosmeier et al., "Determination of the Integral Refractive Index of Cells in Suspension by Digital Holographic Phase Contrast Microscopy", Biophotonics: Photonic Solutions for Better Health Care, Proc. of SPIE vol. 6991, 699110, (2008).

(Continued)

*Primary Examiner* — Gregory M Desire
(74) *Attorney, Agent, or Firm* — Knobbe, Martens, Olson & Bear, LLP (57) ABSTRACT

The current invention concerns a method for detecting cancerous cells and/or classifying cells in a cell sample comprising the following steps:
  providing a cell sample;
  obtaining holographic information from said cell sample by digital holographic microscopy (DHM);
  deriving at least one cellular parameter from said holographic information, and;
  classifying said cells of cells sample;
characterized in that said classification occurs by appointing a Scoring Factor to said cells of cell sample, based on said cellular parameters.

(Continued)

In a second aspect, a system for the detection of cancerous cells and/or classification of cells in a cell sample is provided, employing the method as disclosed in the invention. In a final aspect, a method for updating and/or improving a database comprising thresholds linked to holographic information and the database related thereof is equally disclosed.

26 Claims, 4 Drawing Sheets

(51) Int. Cl.
  *G03H 1/00* (2006.01)
  *G02B 21/00* (2006.01)
  *G02B 21/36* (2006.01)
  *G01N 15/14* (2006.01)
  *G01N 33/483* (2006.01)
  *G06F 17/30* (2006.01)
  *G06F 19/18* (2011.01)
  *G06F 19/28* (2011.01)

(52) U.S. Cl.
  CPC ..... *G01N 33/4833* (2013.01); *G02B 21/0004* (2013.01); *G02B 21/365* (2013.01); *G03H 1/0005* (2013.01); *G06F 17/3028* (2013.01); *G06K 9/00134* (2013.01); *G06K 9/00147* (2013.01); *G03H 2001/005* (2013.01); *G03H 2001/0452* (2013.01); *G03H 2210/12* (2013.01); *G03H 2226/02* (2013.01); *G06F 19/18* (2013.01); *G06F 19/28* (2013.01)

(58) Field of Classification Search
  CPC .............. G01N 33/4833; G02B 21/365; G06F 17/3028; G06K 9/00134; G06K 9/00147
  See application file for complete search history.

(56) References Cited

U.S. PATENT DOCUMENTS

| | | | |
|---|---|---|---|
| 5,243,409 A | 9/1993 | Sagner | |
| 5,256,571 A | 10/1993 | Hurley et al. | |
| 5,495,333 A | 2/1996 | Konda | |
| 6,026,174 A * | 2/2000 | Palcic | G01N 1/30 382/128 |
| 6,249,345 B1 | 6/2001 | Kraack | |
| 6,327,377 B1 | 12/2001 | Rutenberg | |
| 6,361,934 B1 | 3/2002 | Acton | |
| 6,394,966 B1 | 5/2002 | Gill | |
| 6,651,008 B1 | 11/2003 | Vaisberg et al. | |
| 6,809,862 B2 | 10/2004 | Behnsen et al. | |
| 6,924,094 B1 | 8/2005 | Gingeras et al. | |
| 6,954,667 B2 | 10/2005 | Treado | |
| 7,009,700 B2 | 3/2006 | Dubois et al. | |
| 7,286,222 B2 | 10/2007 | Gardner | |
| 7,616,320 B2 | 11/2009 | Javidi et al. | |
| 8,599,383 B2 | 12/2013 | Teitell | |
| 9,569,664 B2 * | 2/2017 | Judkewitz | G06K 9/00624 |
| 9,675,974 B2 | 6/2017 | Jooris et al. | |
| 9,684,281 B2 * | 6/2017 | Mathuis | G03H 1/0005 |
| 2002/0064328 A1 | 5/2002 | Neuberger | |
| 2002/0106119 A1 | 8/2002 | Foran | |
| 2002/0164063 A1 | 11/2002 | Heckman | |
| 2003/0113832 A1 | 6/2003 | Lauf | |
| 2003/0199649 A1 | 10/2003 | Orbison et al. | |
| 2005/0036181 A1 | 2/2005 | Marquet et al. | |
| 2005/0272103 A1 | 12/2005 | Chen | |
| 2006/0014239 A1 | 1/2006 | Luttmann et al. | |
| 2006/0088814 A1 | 4/2006 | Hecht et al. | |
| 2006/0132799 A1 | 6/2006 | Franck et al. | |
| 2006/0283945 A1 | 12/2006 | Excoffier | |
| 2007/0216906 A1 | 9/2007 | Javidi et al. | |
| 2008/0018966 A1 | 1/2008 | Dubois et al. | |
| 2008/0032325 A1 | 2/2008 | DiMarzio | |
| 2008/0113340 A1 | 5/2008 | Schlegel | |
| 2008/0137933 A1 * | 6/2008 | Kim | G01B 9/021 382/131 |
| 2008/0242556 A1 | 10/2008 | Cao et al. | |
| 2008/0304733 A1 * | 12/2008 | Macaulay | G01N 33/5091 382/133 |
| 2008/0317325 A1 | 12/2008 | Ortyn et al. | |
| 2009/0082637 A1 | 3/2009 | Galperin | |
| 2009/0092227 A1 | 4/2009 | David | |
| 2009/0244667 A1 | 10/2009 | Frentz | |
| 2009/0296083 A1 | 12/2009 | Saski et al. | |
| 2009/0305393 A1 | 12/2009 | Joeris | |
| 2010/0034442 A1 | 2/2010 | Minakuchi | |
| 2010/0196871 A1 | 8/2010 | Dodgson | |
| 2010/0315501 A1 | 12/2010 | Ludwig | |
| 2011/0134426 A1 | 6/2011 | Kaduchak | |
| 2011/0204256 A1 | 8/2011 | Patt | |
| 2011/0212440 A1 | 9/2011 | Viovy | |
| 2012/0015391 A1 | 1/2012 | Zhang et al. | |
| 2012/0200901 A1 | 8/2012 | Dubois | |
| 2012/0218379 A1 | 8/2012 | Ozcan | |
| 2014/0038171 A1 | 1/2014 | Roberts et al. | |
| 2014/0049634 A1 | 2/2014 | Tafas | |
| 2016/0160069 A1 * | 6/2016 | Chen | B29C 41/14 428/493 |
| 2016/0231225 A1 * | 8/2016 | Hayden | G01N 15/10 |
| 2017/0023472 A1 * | 1/2017 | Pavillon | A61B 5/0066 |

FOREIGN PATENT DOCUMENTS

| | | |
|---|---|---|
| EP | 1524491 A1 | 4/2005 |
| EP | 2008715 A1 | 12/2008 |
| WO | WO 98/57152 | 12/1998 |
| WO | WO 99/44593 A1 | 9/1999 |
| WO | WO 2004/057464 A2 | 7/2004 |
| WO | WO 2004/102111 A1 | 11/2004 |
| WO | WO 2006/047252 A1 | 5/2006 |
| WO | WO 2007/073345 A1 | 6/2007 |
| WO | WO 2009/051741 A2 | 4/2009 |
| WO | WO 2009/151632 | 12/2009 |
| WO | WO 2009/154558 A1 | 12/2009 |
| WO | WO 2011/042442 A1 | 4/2011 |
| WO | WO 2011/068764 A2 | 6/2011 |
| WO | WO 2011/099925 A1 | 8/2011 |
| WO | WO 2011/154143 A1 | 12/2011 |
| WO | WO 2013/120886 A1 | 8/2013 |
| WO | WO 2014/044823 A1 | 3/2014 |

OTHER PUBLICATIONS

Ling et al., "Application of Flow Cytometry for Biomarker-Based Cervical Cancer Cells Detection," Diagnostic Cytopathology, vol. 36, No. 2, dated 2008.
Wang et al., "Nanoscale Nuclear Architecture for Cancer Diagnosis Beyond Pathology via Spatial-Domain Low-Coherence Quantitative Phase Microscopy," Journal of Biomedical Optics, vol. 15(6), 066028, published Dec. 23, 2010.
Wikipedia, "Quantitative Phase-Contrast Microscopy" retrieved from http://en.wikipedia.org/w/index.php?title=Quantitative_phase-contrast_microscopy&oldid=734365574, last modified on Aug. 13, 2016.
Yeom et al., "Automatic Identification of Biological Microorganisms Using Three-Dimensional Complex Morphology," Journal of Biomedical Optics, vol. 11(2), 0124017, published Mar. 24, 2006.
2014/0193850 including its prosecution history, the cited references, and the Office Actions herein, Jul. 10, 2014, Jooris, et al.
2014/0195568 including its prosecution history, the cited references, and the Office Actions herein, Jul. 10, 2014, Mathuis et al.
2014/0329231 including its prosecution history, the cited references, and the Office Actions, herein, Nov. 6, 2014, Magniette.
2014/0349336 including its prosecution history, the cited references, and the Office Actions herein, Nov. 27, 2014, Magniette.
2015/0056607 including its prosecution history, the cited references, and the Office Actions herein, Feb. 26, 2015, Jooris, et al.

(56) References Cited

OTHER PUBLICATIONS

2015/0248109, including its prosecution history, the cited references, and the Office Actions herein, Sep. 3, 2015, Mathuis et al.
2017/0205222 including its prosecution history, the cited references, and the Office Actions herein, Jul. 20, 2017, Mathius et al.
Beitsch et al., "Detection of carcinoma cells in the blood of breast cancer patients," The American Journal of Surgery, vol. 180, pp. 446-449 (Dec. 2000).
Boulet et al., "Cancer Epidemiology," Biomarkers & Prevention, 2008, 17(4): 810-817.
Daneshpanah et al., "3D Holographic Imaging and Trapping for Non-Invasive Cell Identification and Tracking," Journal of Display Technology, vol. 6(10), pp. 490-499 (Oct. 2010).
Extended European Search Report for European Patent Application No. 16151897.2, dated Jul. 21, 2016.0.
Fook Chiong Cheong et al. "Flow visualization and flow cytometry with holographic video microscopy", Proceedings of the SPIE—The International Society for Optical Engineering SPIE—The International Society for Optical Engineering USA, vol. 7619, 2010, XP040518833, ISSN: 0277-786X. Published Feb. 10, 2010.
Frank Dubois et al. "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.
Fu et al., "Quantitative DIC microscopy using an off-axis self-interference approach," Optics Letters, vol. 35(14), pp. 2370-2372 (Jul. 15, 2010).
Indebetouw, G. et al. Feb. 20, 2007. Scanning holographic microscopy with resolution exceeding the Rayleigh limit of the objective by superposition of off-axis holograms. Applied Optics 46(6): 993-1000. speif. pp. 993, 994.
Kemper, B. et al. Feb. 1, 2008. Digital holographic microscopy for live cell applications and technical inspection. Applied Optics 47(4): A52-A61. specif. pp. A52, 53, 56, 59.
Kemper et al., "Monitoring of laser micro manipulated optically trapped cells by digital holographic microscopy," J Biophoton, vol. 3(7), pp. 425-431 (2010).
Kemper et al., "Investigation of living pancreas tumor cells by digital holographic microscopy," Journal of Biomedical Optics, vol. 11(3), pp. 034005-1-034005-8 (May/Jun. 2006).
Kemper et al., "Simplified approach for quantitative digital holographic phase contrast imaging of living cells," Journal of Biomedical Optics, vol. 16(2), pp. 026014-1-026014-4 (Feb. 2011).
Kemper et al., "Self interference digital holographic microscopy approach for inspection of technical and biological phase specimens," Proceedings of the SPIE—The International Society for Optical Engineering SPIE—The International Society for Optical Engineering USA, vol. 8082, May 23, 2011.
Lee et al., "Incremental feature weight learning and its application to a shape-based query system," Pattern Recognition Letters, vol. 23, pp. 865-874 (2002).
Marin et al., "A meta-index for querying distributed moving object database servers," Information Systems, vol. 35, pp. 637-661 (2010).
McClatchey et al., "Object Databases in a Distributed Scientific Workflow Application," Information Technology, 1997, BIW IT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.
Mihailescu M et al., "Microchannel-pinhole parameters investigation for cells visualization in holographic microscopy", Semiconductor Conference (CAS), 2011 International, IEEE pp. 75-78, XP032069149, DOI: 10.1109/Smicnd.2011.6095718 ISBN: 978-1-61284-173-1. Published Oct. 17, 2011.
Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).
Nenadic et al., "A Possibility of Applying Differential Digital Holography in Manufacturing Process," 48th International Symposium ELMAR-2006, Jun. 7-9, 2006, Zadar, Croatia, pp. 103-106.
Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).
Sahasranuddhe et al., Future Microbiol., 2011 6(9):1-25.
Sun et al., "Visualization of fast-moving cells in vivo using digital holographic video microscopy," Journal of Biomedical Optics, vol. 13(1), pp. 014007-1-014007-9 (Jan./Feb. 2008).
Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).
Weigum et al., "Nano-Bio-Chip Sensor Platform for Examination of Oral Exfoliative Cytology," Cancer Prevention Research, vol. 3, pp. 518-528 (2010).
White et al., "Isolation of Stool-Derived Mucus Provides a High Yield of Colonocytes Suitable for Early Detection of Colorectal Carcinoma," Cancer Epidemiol Biomarkers Prey, vol. 8, pp. 2006-2013 (2009).
Yong-Seok Choi et al., "Lateral and cross-lateral focusing of spherical particles in a square microchannel", Lab on a Chip, vol. 11, No. 3, pp. 460-465, XP55032064, ISSN: 1473-0197, DOI: 10.1039/c01c00212g. Published Feb. 1, 2011.
Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.
International Search Report for Application No. PCT/EP2014/066312, dated Jan. 10, 2014, in 3 pages.
Kosmeier et al., "Determination of the Integral Refractive Index of Cells in Suspension by Digital Holographic Phase Contrast Microscopy", Biophotonics: Photonic Solutions for Better Health Care, Proc. of SPIE col. 6991, 699110, (2008).
Ling et al., "Application of Flow Cytometry for Biomarker-Based Cervical Cancer Cells Detection," Diagnotic Cytopathology, vol. 36, No. 2, dated 2008.
Mann et al., "Dual Modality Live Cell Imaging with Multiple-Wavelength Digital Holography and Epi-Fluorescence," Topical Editor: Dr. Tristan Colomb, 3D Res.2, Accepted: Nov. 3, 2010.
Pavillon, et al., " Cell Morphology and Intracellular ionic homeostasis explored with a multimodal approach combining epifluorescene and digital holographic microscopy," Journal of Biophotonics, vol. No. 7, pp. 432-436, Accepted Mar. 5, 2010.
Pin Wang et al., "Nanoscale Nuclear Architecture for Cancer Diagnosis beyond Pathology via Spatial-Domain Low-Coherence Quantative Phase Microscopy," Journal of Biomedical Optics , vol. 15(6), 066028, dated Nov./Dec. 2010.
Wikipedia "Quantitative Phase-Contrast Microscopy" retreieved from http://en.wikipedia.org/w/index.php?title=Quantitative_phase-contrastmicroscopy&oldid=734365574, last modified on Aug. 13, 2016.
Yeom, "Automatic Identification of Biological Microorganisms using Three-Dimensional Complex Morphology," Journal of Biomedical Optics, vol. 11(2), 0124017, dated Mar./Apr. 2006.

* cited by examiner

METHOD AND SYSTEM FOR DETECTING AND/OR CLASSIFYING CANCEROUS CELLS IN A CELL SAMPLE

CROSS-REFERENCE TO RELATED APPLICATIONS

This application is a continuation of U.S. application Ser. No. 14/233,562, filed Jan. 17, 2014, which is the U.S. National Phase Under 35 U.S.C. § 371 of International Application PCT/EP2012/063936, filed on Jul. 16, 2012, which claims priority to EP 11174583.2, filed Jul. 19, 2011 and PCT/EP2011/070571, filed Nov. 21, 2011, each of which is incorporated in its entirety by reference under 37 CFR 1.57.

TECHNICAL FIELD

The invention pertains to the technical field of diagnostics, and more specifically to a method and system for determining specific parameters of a cell sample by obtaining holographic information by digital holographic microscopy. The method offers a non-destructive manner of analyzing cells and can be used for the detection of cancerous cells and classification of the cells present in a cell sample. Holographic information is obtained and compared to a threshold database relating to cellular parameters. The present invention furthermore discloses a system that employs the method by digital holographic microscopy of the invention as well as a method for updating and/or improving a database comprising thresholds linked to holographic information and the database related thereof.

BACKGROUND

To diagnose whether a patient is suffering from cancer or has a predisposition, cells need to be sampled from a patient and a thorough analysis of the cell sample is required in order to evaluate whether abnormal or aberrant cells are present. Mainly, a pathologist or other skilled medical personnel will base the diagnosis on specific characteristics of the cells in the sample, such as cell morphology, the presence of certain types of cells or proteins and more. These cytological tests are based on a two-dimensional presentation of the cells present in the sample and mostly require the fixation of cells on a substratum and the use of dyes or stainings to visualize specific features of the cells. This is a time consuming and cumbersome work, and requires well-trained specialists. Moreover, as many of the solutions used to fix and stain the cells, this approach will inevitably lead to loss of cell structures and information stored therein. This might thus interfere with the possibility of a reliable interpretation and diagnosis from the sample. Inadequate processing of a sample may lead to an increased number of false negatives diagnoses. For instance, of the over 50 million cervical cytological PAP smears, which are performed in the USA each year, a high false-negative interpretation rate of 20-40% has been described (Williams et al., 1998), frequently leading to fatal consequences. Most of these false negatives are the result of inadequate sample processing.

Since 1990 many advanced technologies focusing on sampling, smear preparation, or screening quality control have been developed and introduced into the practical work to prevent the false negative rate in screening. These commercial devices can be divided into the following categories based on their approaches: (1) for a better slide preparation to reduce sampling error, such as thin-layered liquid based preparation (ThinPrep™, SurePath, Tripath); (2) for reducing workload and screening error, such as autoscreening system (ThinPrep Imaging System, Cytyc, Boxborough, Mass.) and FocalPoint System (Tripath Imaging, Burlington, N.C.); (3) for laboratory quality control, such as rescreening (Papnet); and (4) for quality assurance, such as proficiency test. However, most of these devices are not designed to assist diagnosis by supplying the calculable parameters to eliminate interpretation errors and inter-observer discrepancy. In addition, it is not applicable for general cytological laboratory because of high cost and technical or linguistic gaps. Thus, without a reproducible and quantitative tool, it is still an unsolved problem for a routine cytological laboratory to improve the diagnostic divergence caused by visual observation.

Therefore, the field of cancer diagnosis is in need for methods and devices that analyses cell samples in a non-destructive, non-detrimental and objective manner, or at least provide information of the status of the sample and the cells present prior to its further processing by a specialist. Preferably, the gathered information is obtained by a three-dimensional analysis method in order to perturb the sampled cells to a minimum prior to analysis. Moreover, three-dimensional information will store substantially more cellular data than conventional two-dimensional information. This will undeniably lead to a more reliable diagnosis method as more accurate information will be obtained from the analyzing sample.

U.S. Pat. No. 2,010,006 089 7 discloses a method and device for non-destructive analysis and characterization of a cell sample. The invention makes use of a digital holographic microscope for analyzing certain parameters of a cell and to determine the number of cells in the sample. U.S. Pat. No. 2,010,006 089 7 does not disclose specific parameters to be measured in order to classify a cell as healthy or aberrant. Therefore, the method as disclosed in U.S. Pat. No. 2,010,006 089 7 can be implemented in a diagnostic system, but can serve there merely as an extra tool for gathering information on a sample, and not as the main determining factor whether a sample contains aberrant cells or not.

Choi et al. (2007) from the Massachusetts Institute of Technology (MIT) describes a method based on tomographic phase microscopy to map 3D structures of suspended or substrate-attached cells and to quantify refractive index measurements. By creating overlapping tomograms, a 3D image of a cell could be reconstructed. The authors state that the refractive index data obtained by their described technique can be used to characterize cell sample aberrations. Specific parameters which are suitable to be used in a diagnostic setting are however not disclosed. Moreover, the technique does not generate a real time three-dimensional image, but rather artificially creates a 3D image by superimposing several two-dimensional images captured by the microscope.

Reshetov et al. (2010) present a method to visualize thyroid cancer cells and to study their morphology by atomic force microscopy (AFM). The authors showed a difference in height of the nucleus, height of cytoplasm and ratio thereof of thyroid cancer cells when compared to benign colloidal goiter cells. Disadvantage of the system is the slow scanning speed of the AFM technique, requiring several minutes for one scan. Other disadvantage is the limited area which can be scanned (only micrometer scale, 100×100 µm in X and Y direction, and 10 µm in Z direction) by an AFM as well as the poor image resolution. Moreover, imaging of liquids, for instance cells in solutions, have been proven to be challenging with conventional AFM. These disadvantages make it unlikely that AFM will be widely implemented in oncocytological diagnostic devices.

There remains a need in the art for an improved, non-destructive method for measuring and obtaining specific cellular parameters of cell samples in a three-dimensional manner, which can be used to diagnose the status of the analyzed cell sample. The method should be readily implemented in a cytological screening and diagnosis system and provide a fast, objective and correct analysis of cell samples thereby limiting the requirement of highly trained personnel and man hours which are currently needed to process and analyze each cell sample.

SUMMARY OF THE INVENTION

The present invention provides for a method and system for analyzing cell samples in a non-destructive, fast, inexpensive and objective manner and to detect cancerous cells present in the sample. In the current invention, said cell sample will be analyzed by a digital holographic microscope (DHM) and the practitioner will be provided with a digital report, comprising a set of cellular parameters related to cells present in the cell sample as well as with diagnostic information on the cell sample. This will give the practitioner or pathologist the chance to evaluate the raw sample in an unbiased manner, by taking the provided cell sample parameters into account. Diagnosis can be solely based on the report provided by the system, or if desirable, the practitioner or pathologist can proceed by more conventional means of diagnosing. DHM provides both a highly specific and sensitive method for analyzing cell samples, which is often a problem for other analytical methods currently known. For instance, the PAP smear test, a well-known test for analyzing cervical cell samples, although highly specific, lacks sensitivity. This increases the risk in false negative results, which is to be avoided at all cost.

In a first aspect, the current invention discloses a method for detecting cancerous cells and/or classifying cells in a cell sample as disclosed in claim 1. Preferably, said cell sample is a liquid cell sample.

Digital holographic microscopy enables the study of living cells without the need for markers or dyes, and enables quantitative analysis of the studied cells as well as various sub-sections of said cells by obtaining a three-dimensional image. The possibilities of digital holographic microscopy (DHM) have increased during the last years due to an increase in the development of digital sensors and computers. The methods visualizes cells without any staining up to a degree of cellular and compartment distinguishability which allows efficiently segmenting the cells, counting their number and reliably classify them according to their histological provenience.

In a preferred embodiment of the method according the current invention, at least one cellular parameter is obtained derived from holographic information. A Scoring Factor is appointed to the cells of said cell sample, based on said cellular parameters. Said Scoring factor determines the classification of said cells. Digital holographic microscopy enables a quantitative multifocus phase contrast imaging that has been found suitable for technical inspection and quantitative, three dimensional cell imaging. The holographic information obtained by DHM holds sufficient information in order to classify the cells for diagnostic purpose.

In a more preferred embodiment, at least one cellular parameter derived from obtained holographic information comprises the optical nuclear height. The optical nuclear height, derived from the holographic information, has been found by the inventors to be a highly reliable parameter for detecting cancerous cells. It was found that the optical nuclear height can be correlated to the status of malignancy of said cells.

In a further more preferred embodiment, at least one cellular parameter derived from obtained holographic information comprises cell nucleus diameter, chromatin texture, cell size, cell form and cell morphology. These parameters all will lead to an adequate classification of the cells present in the cell sample.

In a preferred embodiment, after deriving at least one cellular parameter, a Scoring Factor Sc is appointed to each cell, cell type and/or cell sample whereby said Scoring Factor Sc determines the classification of said cells, cell type and/or cell sample. By doing so, each cell is objectively evaluated, ensuring furthermore that all cells essential for diagnosis have been evaluated in the same, objective manner. This is a huge benefit when compared to the analysis of cell samples by a practitioner, as these analysis are often more subjective, and are dependent on the skills and knowledge of the practitioner, as well as to the employed method of analysis and the handling the sample underwent prior to this analysis. Preferably, a practitioner will be provided with a digital report on the classification of said cells in cell sample. After receiving said digital report and diagnostic information stated therein, said practitioner can decide whether it is necessary or not to perform extra analyses, for instance to screen for the presence of a viral infection, e.g. a HPV detection. The extra analysis techniques are preferably based on the detection of a member or combination of members of the following group: Cyclin Dependent Kinase p14Arf, p15INK4b, p16INK4a, p18INKc, p19INK4d, p21WAF1/CIP1 and p27Kip1; cell proliferation marker Ki67, Ki-S5, Ki-S2, MCM2, MCM3, MCM4, MCM5, MCM6, MCM7, Pomfil2, Unc-53, a kinase or phosphatase engaged in the replication process, CDC6, CDC7, CDC7 protein kinase, Dbf4, CDC14, CDC14 protein phosphatase, CDC45, MCM10, a protein engaged in the processive replication fork, a topoisomerase, topoisomerase 2 alpha, PCNA, a DNA polymerase, DNA polymerase delta, replication protein A (RPA), replication factor C (RFC) or FEN 1; HPV genotypes such as HPV genotype 6, HPV genotype 11, HPV genotype 16, HPV genotype 18, HPV genotype 31, HPV genotype 40, HPV genotype 58, HPV genotype 58, HPV genotype c*31, HPV genotype 33, HPV genotype 54, HPV genotype c*33, HPV genotype 35, HPV genotype 39, HPV genotype 40, HPV genotype 42, HPV genotype 43, HPV genotype 44, HPV genotype 45, HPV genotype 51, HPV genotype 52, HPV genotype 53, HPV genotype 56, HPV genotype 74, HPV genotype c*56, HPV genotype 58, HPV genotype c*58, HPV genotype 59, HPV genotype 66, HPV genotype 68, HPV genotype 70, HPV c*68; HPV viral proteins E1-E7, L1-L2. The detection might either imply detection of the presence of a protein or peptide, or detection of DNA, cDNA or RNA.

By providing the practitioner with diagnostic information prior to any handling of the cell sample, time-consuming procedures may be avoided, moreover saving costly man hours for a diagnostic laboratory or service.

Preferably, said appointed Scoring Factor is based upon comparison of said at least one cellular parameter and a threshold database. This threshold database comprises threshold values linked to each derived cellular parameter, whereby these threshold values are indicative of the status of the cells of said cell sample. In a preferred embodiment, said threshold database is stored on an external server. In an even more preferred embodiment, said Scoring factors are appointed by use of queries on said external server.

In a further preferred step of the method according to the current invention, a practitioner will be provided with a digital report comprising Scoring Factors and classification of said cells in cell sample. More preferably, two- and three-dimensional images of said cell sample are provided in said digital report. Based on the holographic information obtained by DHM, three-dimensional and two-dimensional images from the cell sample may be reconstructed. This is again an advantage over the currently known techniques where firstly an image is obtained from a cell sample, mostly a cell sample on a carrier such as a microscope slide, after which quantitative information is calculated. The method and system according to the current invention reconstructs the image after obtaining all necessary quantitative information, being the holographic information, providing a more reliable source of data.

Preferably, the method according the current invention implements an identification step, identifying the cellular type of said cells in the sample, prior to said classifying cells. Identification of the cellular type of the cells in the cell sample occurs based on said cellular parameters derived from holographic information, more preferably based on the cell size. Preferably, this occurs prior to classifying said cells. More preferably, only subsets of cells are classified, whereby said subsets of cells are associated to specific cell types identified in said cell sample. By identifying the cell types prior to classification, only those subsets of cells which are essential to come to a reliable diagnosis of the cell sample can be subsequently classified. This will provide the practitioner afterwards with a digital report which only comprises the most fundamental data, and leaves out redundant information. Furthermore, by only classifying the essential cells, a considerable amount of time is saved during analysis of each sample.

In a preferred embodiment, said cell sample is a cervical sample, preferably a liquid cell sample. In a more preferred embodiment, said cells in said cell sample comprise superficial squamous cells, intermediate squamous cells, basal cells, parabasal cells, red blood cells, macrophages, lymphocytes and micro-organisms. In a further preferred embodiment of the current invention, only said superficial squamous cells, intermediate squamous cells, basal cells and parabasal cells are appointed a Scoring Factor.

In another aspect, current invention provides a system for the detection of cancerous cells and/or classification of cells in a cell sample employing the method according to the current invention, as described in claim 16.

In a preferred embodiment, said system comprises a server, preferably an external server. Said server provides algorithms for the comparison of said cellular parameters with a threshold database.

In another preferred embodiment, said system comprises an exchangeable sample vial comprising identifying indicia. Preferably, said indicia comprise an RFID. Information on RFID tags is stored electronically and is reprogrammable. This way, the practitioner can add or change the information stored on the RFID according to his preferences and according to the procedures utilized in the laboratory where the samples are analyzed.

In a third aspect, the current invention relates to a method for updating and/or improving a database comprising thresholds linked to holographic information, as claimed in claim 21.

In a final aspect, the current invention equally discloses a database of objects comprising holographic information according to claim 28.

DESCRIPTION OF FIGURES

FIGS. 3A-3C depict three-dimensional images of cells in a cell sample, obtained by DHM. FIG. 3A depicts the phase-contrast image of the cell, while

DETAILED DESCRIPTION OF THE INVENTION

The present invention provides for a method and system for detecting cancerous cells in cell samples in a non-destructive manner and to provide information on the cells present in the sample. In the current invention, holographic information will be obtained from a cell sample by a digital holographic microscope (DHM) and based upon the measurement and analysis of certain cellular parameters received from the analysis of this information, a practitioner or pathologist will be provided with a digital report on the status of the cells present in the sample. The latter provides an unbiased report on the status of the cells, and whether aberrant or malignant cells are present. The practitioner will be provided with a fast and objective diagnostic report, after which he can decide whether it is required to analyze the cells ample further by conventional diagnostic methods. As generally is acknowledged, early detection is of utmost importance to survival chances of patients. The method and system according to the current invention provides for a detection tool which can ensure early detection of cancerous or pre-malignant cells in a cell sample obtained by a patient, in an unbiased manner.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the invention provides for a method for the detecting cancerous cells and/or classifying cells in a cell sample comprising the following steps:
  providing a cell sample;
  obtaining holographic information from said cell sample by digital holographic microscopy (DHM);
  deriving at least one cellular parameter from said holographic information, and;
    classifying said cells of cells sample;
    characterized in that said classification occurs by appointing a Scoring Factor to said cells of cell sample, based on said cellular parameters.

The term "sample" as used herein refers to any specimen obtained from a chemical reaction, such as a catalytic reaction, a soil specimen, a specimen comprising microorganisms and/or insects, a forensic specimen or a specimen from a crime scene, such as, but not limited to a hair specimen, body fluids, a water specimen, an entomological specimen.

The term "cell sample" as used herein refers to any specimen obtained from a biological organism, preferably a living organism, which comprises cells from said biological organism. The term relates also to specimen obtained from non-living, i.e. dead biological organisms, in particular recently deceased organisms. In preferred embodiments of the present invention a cell sample may be derived from an animal, preferably from a mammal, e.g. from a cat, a dog, a swine, a horse, a cattle, a sheep, a goat, a rabbit, a rat, a mouse, a monkey. Particularly preferred is a sample obtained from a human being.

In one embodiment, the cell sample comprises cells on a substratum, such as a microscope glass. In another embodiment, said cell sample comprises a tissue sample, such as a biopsy sample. In yet another embodiment, said cell sample is a liquid cell sample. For purpose of the current invention, the term "liquid cell sample" is to be understood as a cell sample in a state of suspension. Said suspension might depend to the nature of the cell sample (e.g. blood, excretions . . . ) or on the nature of preservation of the obtained sample, for instance by adding a buffering solution, or an alcohol.

In one embodiment said cell sample is a tissue sample, a biopsy sample, a brushing or scraping sample from oral cavities, nipple secretions, skin lesions, and eye brushings, a fine-needle-aspiration sample, a smear sample, a mucoid specimens taken from respiratory and gastrointestinal tracts and body fluids such as serous effusions or urinary or cerebrospinal fluids.

In a preferred embodiment, said sample is a smear sample.

In another preferred embodiment, said smear sample is a cervical sample.

The term "holographic information" as used herein refers to the sum of information, generally being phase and amplitude information, which can be obtained through a digital holographic microscope (DHM) from an object or sample. In particular, said holographic information may include 3D and/or 2D images and any information contained herein. In view of the current invention, said sample comprises preferably a liquid cell sample.

Digital Holographic Microscopy (DHM) is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent or a partially coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM), as for instance disclosed in European patent EP 1 631 788. DDHM is different to the other techniques in that it does not really make use of reference and object beams.

The DHM used in the current invention can comprise a conventional digital holographic microscope (DHM), or a differential digital holographic microscope (DDHM). It is to be understood that the use of the term DHM in the current application implies all types of digital holographic microscopes, and is not merely limited to conventional DHM.

The use of DHM in a diagnostic setting has many advantages which makes it the ideal technique to implement in a diagnostic setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological cells, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. Digital holographic microscopy thus makes it possible to visualize and quantify transparent objects and is therefore also referred to as quantitative phase contrast microscopy. More so, DHM allows imaging subcellular structures in three dimensions.

A sample image is calculated at a given focal distance. However, as the recorded hologram contains all the necessary object wave front information, it is possible to refocus an object that was not the plane of focus of the microscope objective. In a DHM system, where the object wave front is recorded from multiple angles, it is possible to fully characterize the optical characteristics of the object and create tomography images of the object.

Furthermore, as some of the DHM systems do not have an image forming lens, traditional optical aberrations do not apply to those DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost.

In view of the current invention, the term 'parameter' is to be understood as a specific characteristic, correlated to a sample, which is obtained or derived from holographic information obtained by digital holographic microscopy. The type of said parameter will depend highly on the nature of the sample, and may relate, but is not excluded to quantitative characteristics, composition characteristics, physical characteristics, chemical characteristics, physicochemical characteristics of said sample.

In a preferred embodiment, when said sample comprises a cell sample, cellular parameters are obtained from the cell sample which relate to the cells and cell types present in said cell sample, said cellular parameters are derived from the quantitative analysis of the holographic information. These cellular parameters will determine the classification of the cell sample, cell types and individual cells. Preferably, the cellular parameters can be derived e.g. by a computer connected to said DHM, in an automated image or hologram analyzing process.

Said classifying cells is to be understood as the classification or ranking of cells in different groups according to their features and characteristics, whereby said features and characteristics are linked to the potential presence of disease, such as cancer, and whereby said features, characteristics and ranked group are an indication of the progression of said disease. Preferably, classification can occur in an automated process e.g. by a computer connected to said DHM.

In a preferred embodiment, the cellular parameter derived by the quantitative analysis of the holographic information obtained by DHM comprises optical nuclear height. In another preferred embodiment, cellular parameter comprises optical height of cytoplasm, the optical height of the nucleoli and any ratio thereof, comprising said optical nuclear height. In a preferred embodiment, the latter are the main indication and/or parameters to classify said cells in a cell sample. The term "optical nuclear height" is to be understood as a distance proportional to the time it takes for light to cross the nucleus in the direction of the height and depends on both the physical height as the optical properties of the nucleus, in particular its, possibly averaged, refraction index. In this document, whenever absolute numbers are used to denote the optical nuclear height, the proportionality constant is the speed of light in vacuum, unless the context dictates otherwise. Furthermore, unless explicitly stated otherwise, the optical nuclear height is expressed in this document with reference to the optical height of the liquid medium, in which case it is proportional to the difference of the time it takes for light to cross the nucleus in the direction of the height and the time it takes for light to cross the same distance in the liquid medium. In general, one can define the optical nuclear height as the result obtained by multiplying the refractive index multiplied with the actual physical height.

The inventors have found that the optical height of the cell nucleus is correlated to the malignant state of the cell. Pre-malignant and malignant cells were seen to have a greater optical height when compared to normal, benign cells. As such, the parameter optical nuclear height, or any ratio comprising optical nuclear height, can be used to discriminate between normal, healthy cells, and cells which display aberrant features, often related to malignancy.

In a further preferred embodiment, other cellular parameters derived from said holographic information comprise cell quantity, nuclear size, nuclear volume, nuclear size variability, nuclear volume variability, chromatin texture, cell size, cell form or shape and cell morphology or any combination thereof such as ratios.

The term "cell morphology" as used herein refers in general to the form, structure and configuration of a cell and may include aspects of the cell appearance like shape, color or pattern of internal or external part of a cell.

The term "form or shape of a cell" as used herein refers to typical cell forms like circular cells, elliptic cells, shmoo like cells, division forms like dumbbells, star-like cell forms, flat cells, scale-like cells, columnar cells, invaginated cells, cells with concavely formed walls, cells with convexly formed walls, the presence of prolongations, appendices or cilia, the presence of angles or corner etc. Typical morphologies or forms would be known to the person skilled in the art and can be derived from Junqueira et al., 2002, Basic Histology, Mcgraw-Hill editors.

The term "cell size" as used herein is to be understood as the physical dimensions of the cell, mainly the surface area of the cell.

The term "nuclear size" is to be understood as the surface area of the cell nucleus and the form that said cell nucleus adopts, being typically circular or elliptical.

The term "nuclear size variability" as used herein is to be seen as the variability of the statistical distribution of all nuclear sizes analyzed.

The term "chromatin texture" as used herein is to be understood as the granulometric characteristics of the chromatin in the nucleus.

In one embodiment of the current invention, the parameters nuclear size, nuclear size variability, chromatin texture, cell size, cell form or shape and cell morphology are the only cellular parameters used to classify said cells, cell types and cell sample.

In a more preferred embodiment, the parameter optical nuclear height, or any ratio comprising the optical nuclear height and a second parameter are utilized for classification of said cells, cell types and cell sample.

In a preferred embodiment, next to the parameter optical nuclear height, said obtained parameters nuclear size, nuclear volume, nuclear size variability, nuclear volume variability, chromatin texture, cell size, cell form or shape and cell morphology are equally utilized in order to classify said cells, cell types and cell sample.

Figure 1:
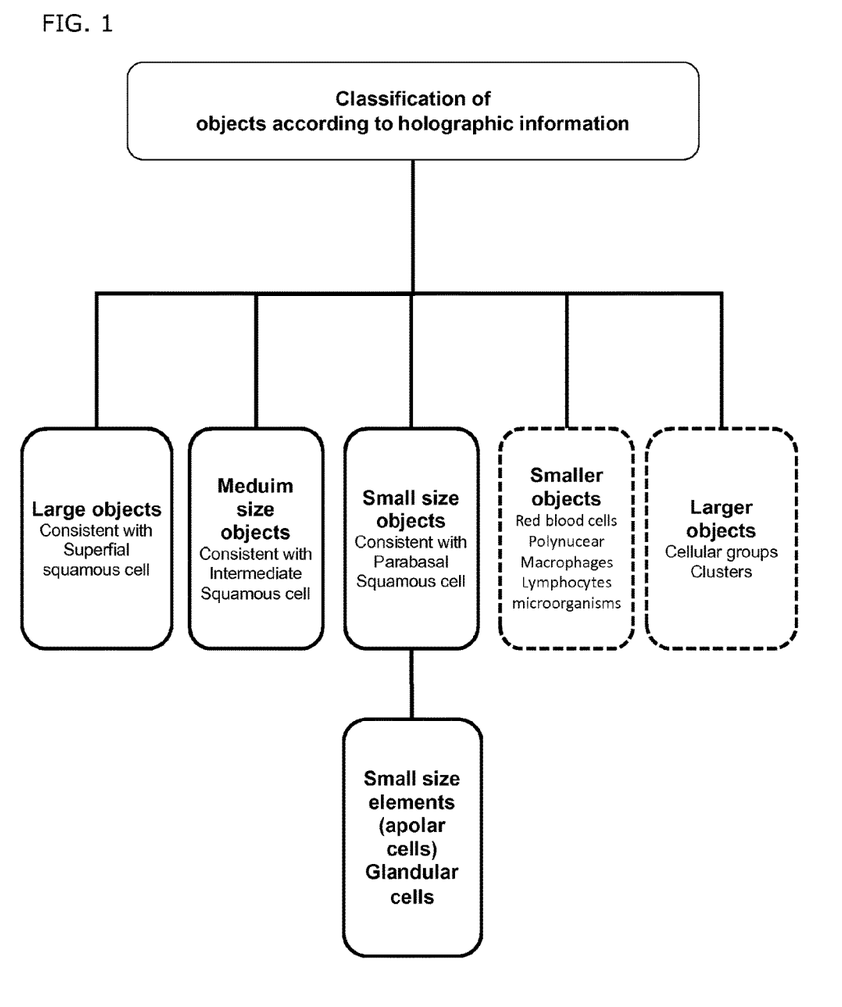
FIG. 1 depicts a schematic overview of a one embodiment of the current invention, whereby cells of a cell sample, in the current example a cervical sample, are identified by a cellular parameter.

In a preferred embodiment, said cells of cell sample will be identified prior to the classification of cells. It should be apparent to any person skilled in the art that identification of cells can occur based on various parameters. In a more preferred embodiment, said identification occurs through the cellular parameter cell size. A system deploying the method according to the current invention can be pre-set as to only classify a certain predefined subsets of cells present in said cell sample, whereby said subsets of cells are associated to specific cell types identified in said cell sample, and to ignore categorizing cells which do not belong to said predefined subsets. In a preferred embodiment, said predefined subset of cells are these cells which are crucial for the analysis of the cell sample and diagnosis related thereon, while the other, non-analyzed cells, are to be considered as redundant. For instance, cells such as blood cells are irrelevant for the detection of the presence of cancerous cells. Hence, in a preferred embodiment, only subsets of cell types identified in cell sample are being classified. For instance, in the preferred case where the cell sample comprises a cervical sample, said majority of cells in the cell sample can be identified as superficial squamous cells, intermediate squamous cells, basal cells and parabasal cells. The remaining cells comprise red blood cells, macrophages, lymphocytes and micro-organisms. The method according to the current invention, and related system thereof, can be pre-set to only classify and appoint a Scoring factor to said superficial squamous cells, intermediate squamous cells, basal cells and parabasal cells, as these are the ones which are essential to come to a diagnosis of the cell sample. FIG. 1 depicts a decision tree according to an embodiment of the current invention to identify the cellular type of the cells present in the cell sample, whereby said cell sample is a liquid cervical sample and whereby said cells are identified through the cell size parameter obtained by DHM. Preferably, cells are identified as belonging to a certain cell type. In the case of a cervical sample, these cell types comprise superficial squamous cells, intermediate squamous cells, parabasal cells, basal cells, glandular cells and red blood cells, lymphocytes, macrophages. The latter three types are of lesser importance when detecting cancerous cells. Preferentially, cells will be identified by predefined set of thresholds relating to the cellular size. For instance, elements or cells with a cell size equal or above 45 µm are consistent with superficial squamous cells; cells with a cell size between 30 and 45 µm are consistent with intermediate squamous cells; cells with a cell size between 15 and 30 µm are consistent with basal, parabasal and glandular cells. Cells and elements larger than 15 µm are consistent with red blood cells, lymphocytes, macrophages, lymphocytes and microorganisms. Although the latter will not be classified, these cells will preferably be counted, as their abundant presence, especially of lymphocytes, might be an indication of inflammation being present.

In yet another embodiment, said obtained cellular parameters are compared and correlated to a threshold database comprising a set of thresholds related to known cellular parameters in order to classify said cells. The term "threshold database" as used herein refers to any suitable collection of reference information or reference parameters related to a sample. In the case said sample comprises a cell sample, said threshold database comprises at least one of the above mentioned parameters and may include data on cell size, cell morphology, number of cells in a defined area, optical density of the nucleus of cell, optical height of nucleus, optical height of the cytoplasm, ratio between optical height nucleus and cytoplasm, ratio between cytoplasm and nucleus of a cell, color of a cell, color of a nucleus, color of a cell wall, number and form of internal cellular structures like the number and form of vacuoles, the number and form of mitochondria, division related structures like chromosomal structures, form, size, morphology of the nucleus and/or the location of the nucleus within the cell, association of cells, the degree of independence of cells, volume of a cell, proportion of the length of the cell wall to the cell size, number of identical or similar cells in an image, or number of ruptures, fissures, holes or visible pores in a cell. The corresponding information may be stored in any suitable format. The reference parameters or the reference information may be stored in the form of predefined threshold values, which allow a fast and reliable comparison of measured values with predefined default values. Once such threshold values are not met, an alert or information signal may be generated informing the practitioner or operator about a sub-optimal or not met parameter criterion. In one embodiment, said threshold database stores different sets of thresholds, which relate to the same obtained parameter, but which take the inherent characteristics of the sample which can have an impact on the correct analysis of the sample into account. For instance, a different set of thresholds can be stored, related to the media used in the sample. As the refraction index of these media can differ, also the obtained parameters will differ. By providing different sets of thresholds that take the latter into account, aberrant analysis of the sample is avoided.

In one embodiment, a Scoring factor is appointed to a sample of constituents of said sample, based upon the comparison of the obtained parameters with said threshold database. Said Scoring Factor is a measure for to the current status, identity, fingerprint, quality, nature, type and/or class of said sample. Said Scoring Factors are appointed by use of queries.

Figure 2:
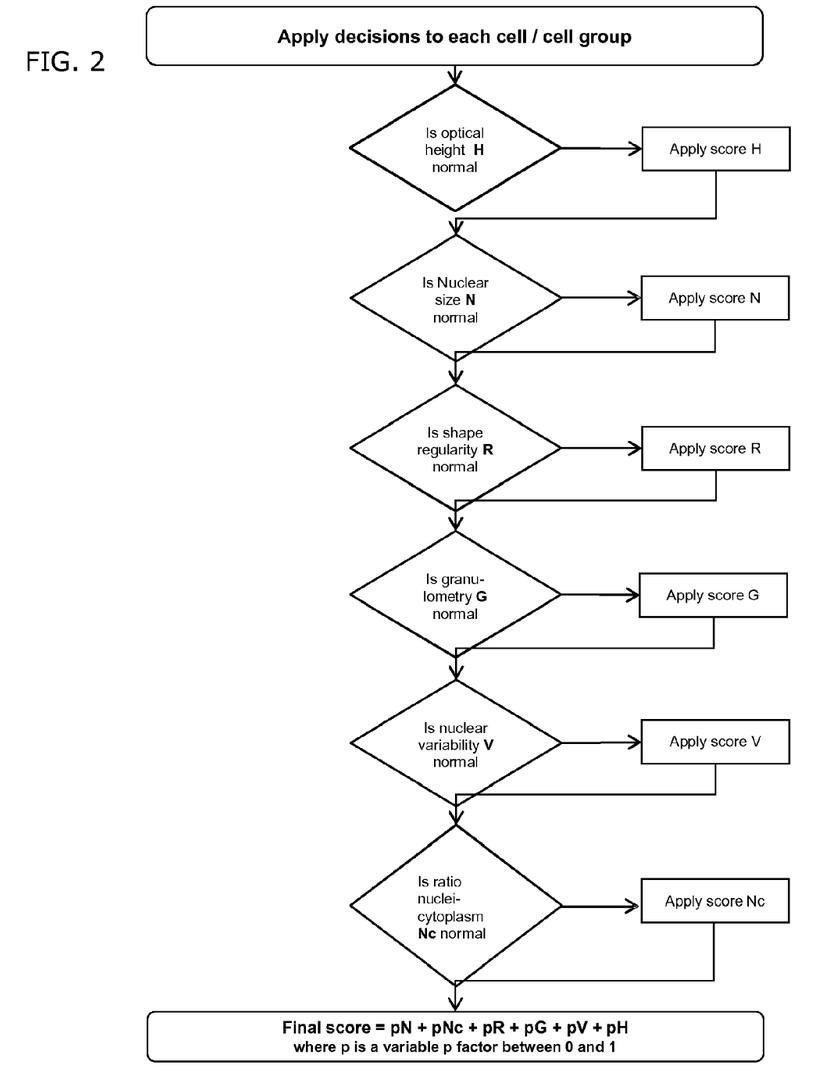
FIG. 2 depicts an exemplary decision tree according to embodiments of the current invention, used to classify cells in a cell sample.

In a preferred embodiment, a Scoring Factor is appointed to the cells based upon comparison of said at least one cellular parameter and a threshold database. Said threshold database is linked to the holographic device. In one embodiment, said threshold database can be stored locally on an internal server, for instance directly accessible by the practitioner analyzing said cell sample. This way the practitioner can consult his own version of the database stored on his computer or internal server. In a more preferred embodiment, said threshold database is stored on an external server, which requires sending the obtained holographic information to said external server. Said Scoring Factors are appointed by use of queries on said internal or external server. In another more preferred embodiment, said database and queries are applicable for cloud computing and being stored and/or computed in the cloud. FIG. 2 depicts a decision tree according to embodiments of the current invention for classification of the cells present in the liquid cervical cell sample. Classification occurs by taking into account the obtained parameters through DHM. In a preferred embodiment, said classification occurs only on a predefined subset of cellular types present in said cell sample.

In a further embodiment, said each cell, cell type and/or cell sample is appointed a Scoring Factor Sc based upon comparison of said obtained cellular parameters and said parameters from threshold database, said Scoring Factor Sc determines classification of cells, cell types and/or cell sample, specifically in relation to a disease. The Scoring Factor Sc is defined as a numerical value or diagnostic status appointed to a certain cell, cell type or cells sample and which said numerical value or diagnostic status is based on a comparison of obtained parameters linked to said cells, cell types and/or cell sample with a threshold database. Said Scoring Factor is to be seen as a general indication of the status of a cell, preferably in relation to the presence or absence of disease, such as cancer.

In a preferred embodiment, said appointed Scoring Factor is a diagnostic status whereby cells, cell types and cell sample can be subdivided in three subgroups, being benign, undetermined and dysplastic or malignant. For the purpose of the current invention, the term benign is to be understood as normal and not displaying any abnormalities, and hence not to be seen as an indication of disease being present or risking to be developed. The term malignant or dysplastic is to be understood as containing clear features and characteristics which are to be considered as abnormal or aberrant, especially compared to a reference set of cells, cell parameters or thresholds. Presence of malignancy is a clear indication of the presence or development of disease. The term undetermined is to be understood as being atypical, comprising characteristics of both benign and malignant. Abundant presence of undetermined cells in a sample will often require a second analysis of the sample by a practitioner in order to correctly diagnose the cell sample. In the case said cell sample is a cervical sample the said undetermined cells are labeled as ASCUS cells. The presence of ASCUS cells might be an indication of the pre-malignant state of the cells, but might equally be a sign of vaginal or cervical inflammation or infection such as a HPV infection. The presence of ASCUS cells requires further diagnostic tests of examination by a pathologist.

In another preferred embodiment, specifically when said cell sample is a cervical cell sample, said appointed Scoring factor is a diagnostic status whereby cells, cell types and cell sample can be subdivided in subgroups, said subgroups being normal, (Cervical Intraepithelial Neoplasia) CIN1, CIN2, CIN3 or CIN4.

In another preferred embodiment, said Scoring Factor is related to the Bethesda Scoring System (1988, 1991 or 2001).

In another embodiment, said Scoring Factor can be related to other staging systems generally known by a person skilled in the art to stage cancer cells and cancer types. Examples of other staging systems are for instance the TNM (Tumor, Node, Metastasis) staging system, the Ann Arbor staging system, Cotswold System, FIGO system.

In one embodiment, said appointed Scoring Factor is solely based on the optical nuclear height of the cells or a ratio comprising said optical nuclear height parameter. A Scoring Factor will be appointed to an identified cell, when compared to the pre-set threshold of optical nuclear height. In a preferred embodiment, said cervical cells are classified as benign when they display an optical nuclear height between 0.1 and 0.4 µm, while cells with an optical nuclear height between 0.5 and 1 µm are classified as malignant. Cells with values between 0.4 and 0.5 µm are classified as undetermined.

In another embodiment, the Scoring Factor Sc may be appointed as the sum of ponderation factors px, whereby said ponderation factors px are directly correlated to a specific cell parameter obtained by DHM. Scoring factor Sc may in one embodiment be defined by the formula:

$$Sc=pN+pNc+pR+pG+pV$$

Whereby px is a ponderation factor associated with the importance of factor to define the cell as being malignant, and whereby:
  pN relates to the nuclear size of a cell. If the ratio of nuclear size and cytoplasm size of a cell is normal, then pN equals 0, if not, then pN equals 1.
  pNc relates to the ratio between nuclei and cytoplasm of a cell. If this ratio equals 0.5, then pNc equals 1, if not, then pNc equals 0.
  pR relates to the shape of a cell. If this shape is regular, then pR equals 0, if not, then pR equals 1.
  pG relates to the granulometry of the chromatin. If this granulometry is homogenous, then pG equals 0, if not, then pG equals 1.
  pV relates to the variability of nuclear size of a cell. If this variability is regular, then pV equals 0, if not, then pV equals 1.

Said Scoring factor is determined for each cell which is evaluated by DHM.

In a preferred embodiment, depicted in FIG. 2, said Scoring Factor is defined as:

$$Sc=pN+pNc+pR+pG+pV+pH$$

whereby pH relates to the optical nuclear height of said cell. If the optical height is regular, than pH is 0, if not, then pH is 1.

In the embodiment where the appointed Scoring Factor subdivides cells in said subgroups benign, undetermined or malignant, the following classification is concluded:
  if Sc equals 0 then said analyzed cell is considered benign;
  if Sc equals 1 or 2, then cell is considered undetermined, and finally;
  if said Sc equals or is more then 3, then said cell is considered dysplastic or malignant.

It should be apparent to a person skilled in the art that the latter is merely to be understood as an embodiment of the current invention, and that the said Scoring Factor may be defined in various ways, according to the preferred staging system.

In another embodiment, said current invention may be used for fingerprinting of cells in a cell sample, whereby said Scoring factor is to be understood as an identity card or for instance a factor, such as a number, unambiguously linked to such an identity card of the cells given to the practitioner, based upon comparison of the obtained parameters of said cell with the stored parameters of various sorts of cells in the database. The latter allows for instance to identify all different cells present in a cell sample based on a collection of obtained parameters. Said collection of obtained parameters is compared to a predefined set of parameters in the database, whereby each predefined set correlates to one specific cell type or cell identity. This way, fingerprinting or identification of the cells in a cell sample is possible.

In a preferred embodiment, a practitioner will be provided with a digital report, based on the holographic information and its processing, comprising Scoring Factors of each analyzed cell as well as a Scoring Factor per cell type and a general Scoring Factor linked to the whole cell sample. Said Scoring factor for each cell type and for the whole cell sample is derived from the individual Scoring Factors appointed to the individual cells. The digital report comprises a diagnostic evaluation of the cell sample, whereby the term diagnosis in the context of the current invention is to be seen whether or not malignant or pre-malignant cells are present in the cell sample according to the classification of the cells based on the parameters obtained by DHM and said Scoring Factor. Preferably, said digital report will signalize the presence of malignant and/or undetermined cells to the practitioner, as well preferably provide information on the cell types of each classified cell. Furthermore, the digital report will provide the practitioner with the parameters obtained by the DHM image analysis, on which identification and classification is based. Preferably, said digital report will equally compare each obtained parameter with the corresponding thresholds stored in said threshold database. Said digital report equally comprises images of the analyzed sample, and cells present in said cell sample. Preferably, said images comprise three-dimensional and two-dimensional images derived from said holographic information. The latter allows the practitioner to evaluate the cells both visually and objectively by a combination of said images and said parameters and Scoring Factors. Said threshold database can be stored locally on an internal server accessible by the practitioner.

Figure 3A:
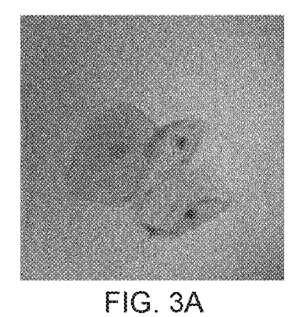
Figure 3B:
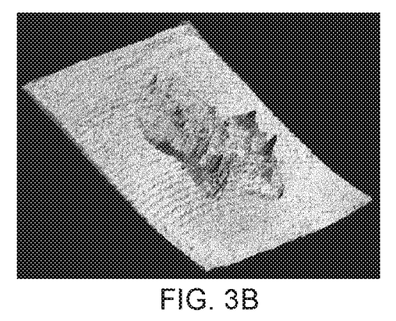
FIG. 3B shows the three-dimensional image from the same field of cells, obtained by DHM.
Figure 3C:
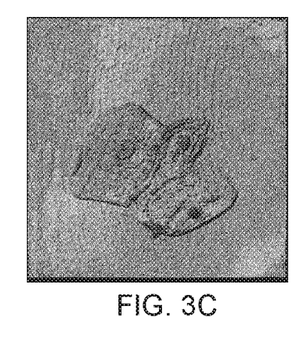
FIG. 3C is a top-view of the cells, obtained by DHM.

In a preferred embodiment, said holographic information obtained in the lab of the practitioner by DHM is sent to an external server. The external server might be a server on a location distant from the location of the practitioner. Preferably, said external server is being stored and/or computed in the cloud. Said external server stores the threshold database and the algorithms for analysis of said holographic information, cellular parameters. Said analysis of holographic information may comprise identification, classification and quantification of cells in cell sample. In a subsequent step, the results of said analysis are sent back to the practitioner in the form of a digital report. Said digital report comprises the Scoring Factors and classification of said cells in cell sample, preferably also the two- and three-dimensional images of said cell sample. Thus, the practitioner is simultaneously presented with the diagnostic analysis of the cell sample, the cells and cell types present therein, preferably also three- and two-dimensional images related thereof. Said digital report presents a diagnostic tool for the practitioner to evaluate the cell sample. In a preferred embodiment, the practitioner will be presented with a digital overview of the cells present in the cell sample by means of a scatter plot, whereby each analyzed cell presents a dot or point in said scatter plot. In a preferred embodiment, the cell types of the cell sample are plotted along the vertical axis of said scatter plot, while the Scoring Factors related to said cells are plotted along the horizontal axis. This way the practitioner gets an immediate overview of the status of the cell sample and the number of cells which are appointed to a certain Scoring Factor as well to which cell type they belong. A zoom function is provided, which allows said practitioner to zoom in on said scatter plot, permitting to analyze the dots representing cells more in detail. Zooming will result in the presentation of the 3D and 2D images to the practitioner linked to said cells and/or cell populations, presented by said dot on scatter plot. FIG. 3 represents an example of images related to cells in a sample obtained by DHM which may be shown to the practitioner. FIG. 3A depicts the phase-contrast image of the cell, while FIG. 2B shows the three-dimensional image from the same field of cells, obtained by DHM, depicting the height of the nucleus. FIG. 3C is a top-view of the cells, obtained by DHM. Simultaneously, when zooming in on certain cell or subpopulation of cells, the practitioner will be presented with the parameters linked to said cell and/or subpopulation, as well as with the Scoring Factor related thereof. In a more preferred embodiment, said practitioner presented with the analysis can indicate whether in his opinion, the Scoring Factor appointed to said cells, cell types, cell sample matches with his diagnosis. This opinion will be resend to said external server where the opinion of the practitioner can be compared to the opinion provided by the server. The latter will serve as a constant quality control of the threshold database and the algorithms used for analysis and provides for a dynamic system as the threshold database and the algorithms will be constantly adapted and updated, based on the findings of said practitioners. As such, an intelligent, self-sustaining database is created.

In another, more preferred embodiment, the method according to the current invention will allow the concept of "collaborative diagnostics". For the current invention, the term "collaborative diagnostics" is to be understood as a diagnostic method, whereby the diagnosis of a sample, preferably a cell sample, is retrieved by a collaboration of professionals in a relevant field of interest (e.g. pathologists, medical doctors, scientists, etc.), whereby each said professional is able to give an opinion or state a diagnosis related to the sample, based on the data retrieved by the DHM and the digital report. Said professional can be independent and does not have to be professionally linked to the patient, cell sample or practitioner that obtained the cell sample. Said professional can retrieve the data from a remote location (a collaborative diagnostic platform) and provide an independent opinion/diagnosis on the status of the sample. Said diagnosis is then communicated to the practitioner in charge of the final diagnosis of the sample and/or to other professionals, member of the collaborative diagnostic platform. As such, the final diagnosis may be based on both the opinion/diagnosis of the practitioner directly related to patient and sample, and on the opinion/diagnosis of the external professionals.

Preferably, said threshold database will be an intelligent, self-sustaining database, based on the input from the practitioner and from professionals providing an opinion/diagnosis on said sample.

Preferably, for the purpose of the current invention, each image obtained by DHM will receive image identification. Said image identification is to be understood as an identification tag or code uniquely linked to an obtained image and/or to the objects in the image, said objects are preferably cells, and serves as recognition tool for said image and/or objects of image. More preferably, said image identification comprises also positional information, such as position coordinates. For instance, when each object within an image is provided with image identification, then said image identification will comprise the coordinate information of each object within that image. The image identification is sent to the external server together with the parameters obtained by DHM, whereby said all parameters derived from a specific image and/or the objects within an image are linked uniquely to the image identification. For instance, all parameters derived from one certain image will comprise and be linked to one image identification, said image identification corresponds uniquely to that one image. Alternatively, all parameters, derived from one object, within an obtained image, such as a cell, may comprise and be linked to an image identification, which uniquely correspond to said object within image. When said Scoring Factors are computed from the obtained DHM parameters, said each obtained Scoring Factor will subsequently be linked to the image identification of said parameters used to derive said Scoring Factor. Scoring factors and corresponding image information are then communicated back to the practitioner. By linking said Scoring Factor unambiguously to the image identification, the practitioner will be able to relate the presented Scoring Factor directly to the basis image and or objects within that image, which served as a basis for the computed Scoring Factor. Preferably, said scatter plot and each dot representing a cell will unambiguously be linked to image identification.

In a second aspect, the current invention discloses a system for the detection of cancerous cells in a cell sample which employs the method according the current invention.

Said system comprises preferably:
 a digital holographic microscope (DHM) comprising illumination means, an interferometer and a digital recording device connected to a server;
 at least one exchangeable sample vial or sample carrier comprising a cell sample; and
 a computer or printer capable of providing a digital report related to said cell sample.

In one embodiment, said server is an internal server. In a preferred embodiment, said server is an external server, providing algorithms for the comparison of said cellular parameters with a threshold database.

The system of the current invention is ideally suited for analyzing a large number of cell samples in a fast, reliable, accurate and very complete way. Samples may be provided on a carrier (for instance a microscope slide) or in a sample vial. Preferably, said sample vials have known dimensions such that they easily fit in the movable sample vial holder. The thickness of the sample vials is also determined such that the front focal plane of the digital holographic microscope automatically falls within the cell sample, without the needs of refocusing the microscope for each sample. The sample vial holder can then be moved, e.g. rotated or translated, to position the sample vial with the cell sample essentially in the front focal plane of the objective lens of the interferometer. After taking the necessary holographic images, the sample vial holder with sample vial may be moved away. At the same time or subsequently, another sample vial in the same or another sample vial holder may be moved to position the sample vial with the cell sample essentially in the front focal plane of the objective lens of the interferometer. In a preferred embodiment, the system comprises a sample vial, whereby said sample vial comprises a material which is transparent for the illumination beam of said illumination means.

In another embodiment, a disposable micro-optical (D)DHM sensor is embedded in the sample vial itself, providing a sole entity for carrying the liquid cell sample and analyzing said vial content by (D)DHM.

In another embodiment, the system for analyzing a cell sample comprises a sample vial or sample carrier which has identifying indicia, said indicia may be fixed indicia and/or programmable indicia. Said indicia correlate to the patient's identity and/or vial's identification and are preferably machine-readable. In one embodiment, said indicia comprise a bar code label, which corresponds to and uniquely identifies the vial and the sample contained therein. In a most preferred embodiment, said indicia comprise an RFID tag. Said RFID tag can be linked to patient information and/or to a numerical code which correlates to patient information of the database of said practitioner. When holographic information linked to said cell sample is sent to the server, said identification information derived from the indicia is equally sent along. In a preferred embodiment said identification information is linked to information stored in the RFID and/or information provided by the practitioner. In a most preferred embodiment, said identification information is anonymous, and does not comprise information that can be linked to the identity of the patient, hence ensuring his privacy. Said identification information can be linked to the vial, for instance by a code pre-set by the manufacturer or supplier. Preferably, the provided identification information comprises a numerical code, sex, age and/or geographic location of said patient. Preferably said identification information may equally comprise information on the inherent characteristics of said sample. For instance, when said sample being a liquid cell sample, identification information might comprise information on the medium being used for preserving and fixing the cell, as well as for instance on the refraction index of that medium or liquid (in the case of for instance blood, secretions, or urine). This information can be important for the queries that are launched subsequently in order to obtain said Scoring factor related to the sample and objects in sample. Hence, said threshold database can store groups of thresholds and parameters, precisely related to these inherent characteristics of the sample which can have an impact on a correct analysis (such as refractive index of the medium). Simultaneously, the used set of queries can equally be adapted to these inherent characteristics of the sample. By informing the system of such characteristics through the identification information, or manually through the practitioner, faults in analysis will be avoided. Alternatively, when informing the system of such inherent characteristics, the system can correct the obtained parameters to the 'default' state of the thresholds stored in the database, hence avoiding aberrant results when comparing the parameters to these thresholds.

In order for the system to maintain an association between each sample vial or carrier and the corresponding holographic information and digital report, preferably an identification correlation system is provided. The indicia are read by identifying means, such as a laser scanner bar code reader in the case of the indicia being a bar code, or a RFID reader when indicia being an RFID tag. Additionally, information related to the date and time of the obtained holographic information can be added, in addition to the initial sample indicia. Optionally, the name or other identifier of the cytological laboratory analyzing the sample with the system may be linked to the identification information as well.

In a more preferred embodiment, the system for analyzing a cell sample comprises a computer or printer capable of providing a report based on the comparison of said holographic information, said parameters obtained thereof and said threshold database, whereby said report is correlated with said indicia on said sample vial. As mentioned previously, the identification information send together with the obtained holographic information to the server keeps the correlation to the sample, sample vial or carrier and eventually created digital report.

It is obvious that the acquisition of a holographic image requires illumination means. In the present embodiment, the light from these illumination means may comprise spatially and temporally partially coherent light, as well as highly correlated laser light. Spatially and temporally partially coherent light can be produced by e.g. a LED. A LED is cheaper than a laser and produces light with a spectrum centered around a known wavelength, which is spatially and temporally partially coherent, i.e. not as coherent as laser light, but still coherent enough to produce holographic images of the quality which is necessary for the applications at hand. LEDs also have the advantage of being available for many different wavelengths and are very small in size and easy to use or replace if necessary. Therefore, providing a method and system which can use spatially and temporally partially coherent light for obtaining holographic images will lead to more cost-effective devices for implementing such a method.

In another aspect, the invention provides for a method for updating and/or improving a database comprising thresholds linked to holographic information, comprising the steps of:
- obtaining holographic information linked to a sample characterized in that said holographic information is obtained using digital holographic microscopy (DHM);
- deriving at least one parameter from said holographic information;
- comparing said parameter to said thresholds stored in database;
- computing a Scoring Factor based on said comparison of said parameter and said thresholds;
- reporting said Scoring Factor to a practitioner;
- obtaining feedback of said practitioner with regards to said Scoring Factor; and
- updating said database on the basis of said feedback.

The latter allows for a constant updating and optimizing of the thresholds used for computing said Scoring Factor, resulting in more trustworthy results. As such, an intelligent, self-sustaining database is created. The current method might equally be part of the 'Collaborative diagnostics' concept, whereby input regarding a sample is obtained by the practitioner directly involved with the sample and by independent professionals, member of the collaborative diagnostic platform.

Preferably, said holographic information is sent to a server for said deriving at least one parameter and/or computing said Scoring Factor. Said server provides queries for deriving at least one parameter and/or computing Scoring Factor. In another embodiment, said database and queries are applicable for cloud computing and being stored and/or computed in the cloud. In a preferred embodiment, these queries can be adapted based on said feedback of practitioner (intelligent, self-sustaining database)

In a preferred embodiment, said specimen is a cell sample, more preferably a liquid cell sample.

In a more preferred embodiment, identification information linked to the sample is equally stored in said database. Said identification information may comprise the date of sampling, the nature of the sample, the lab analyzing the sample. In the case where the specimen is taken from a living entity, such as an animal of a human being, said identification information may comprise information linked to the identity of said entity.

In another preferred embodiment, image identification linked to said holographic information and/or parameters is stored in said database.

Preferably, said cells present in said cell sample are identified and/or classified based upon the computed Scoring Factors.

In a further aspect, the current invention relates to a database of objects comprising:
- holographic information obtained from a sample comprising objects using digital holographic microscope and/or parameters derived thereof;
- thresholds and queries related to said thresholds for the analysis of said holographic information and/or parameters;
- Scoring Factors derived from said holographic information and/or parameters;
- image identification;
- identification information; characterized in that said thresholds and queries of database are updated based upon receiving feedback information from a third party.

Said third party is to be understood as the party receiving the Scoring Factors and digital report related to the analyzed sample and who will further analyze said sample based upon the received information and results from the analysis of the holographic information. The third party is able to autonomously analyze said sample and compare the results of the database analysis with its own findings. Preferably, said third party is able to send feedback to the external server and database. Based upon this feedback, the queries and thresholds used for the analysis of holographic information and/or the parameters related thereof may be updated or adapted.

Preferably said holographic information and/or parameters derived thereof are linked to identification information and/or image identification.

The present invention will be now described in more details, referring to experimental data and examples that are not limitative.

Example 1

16 selected patients previously diagnosed by the Thinprep® liquid based cytology confirmed by HPV Abott® assay or histology diagnosis for CIN2/3, were analysed on the new Holocyt® diagnostic intelligence software by use of the Holographic Digital Microscope (DHM) using partially coherent laser light.

DHM enables a quantitative multifocal phase contrast imaging that has been found suitable for quantitative and qualitative inspection, and for 3-dimensional cell imaging. 188 cells were identified and measured in an automated way. Nucleus/Cell Ratio (NCR) and Optical Height Delta (OHD) were extracted in the 3D holographic image. The Optical Height Delta is the difference between Nucleus top height minus Cytoplasm average height. NCR and OHD were separately determined in 2 groups: CIN1 or CIN 2/3 patients.

These results were compared with normal cells either from patients with normal cytology diagnosis either from normal cells within the abnormal smears. Data were imported in the global data sheet and statistical ROC analysis and Area Under de Curve (AUC) were performed.

|  | Negative | Positive | p value ANOVA | AUC (ROC) |
|---|---|---|---|---|
| CIN1 | | | | |
| n | 66 | 122 | | |
| NCR | 0.30 +/− 0.23 | 0.39 +/− 0.17 | 0.002 | 0.71 |
| OHD | 0.22 +/− 0.09 | 0.34 +/− 0.14 | <0.0001 | 0.75 |

-continued

|  | Negative | Positive | p value ANOVA | AUC (ROC) |
|---|---|---|---|---|
| CIN2, 3 |  |  |  |  |
| n | 83 | 105 |  |  |
| NCR | 0.29 +/− 0.21 | 0.41 +/− 0.17 | <0.0001 | 0.76 |
| OHD | 0.23 +/− 0.10 | 0.35 +/− 0.14 | <0.0001 | 0.75 |

Figure 4A:
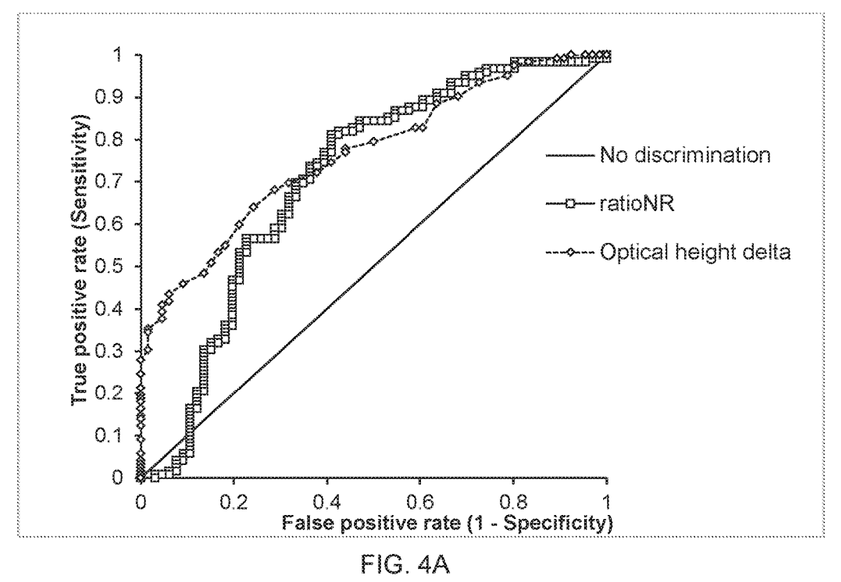
FIG. 4A depicts a graphical overview of results obtained by the method according to the current invention, for cervical cells with diagnostic status equal to or higher than CIN1.
Figure 4B:
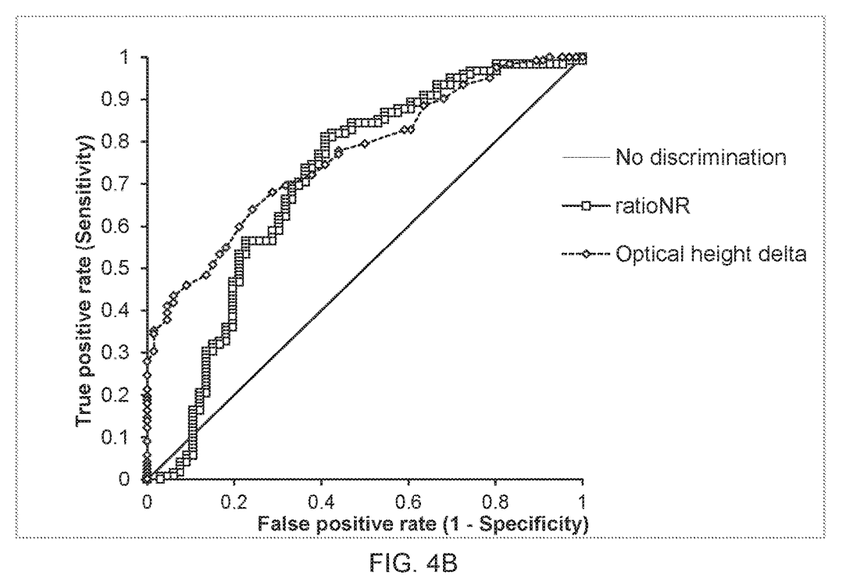
FIG. 4B depicts a graphical overview of results obtained by the method according to the current invention, for cervical cells with diagnostic status equal to or higher than CIN2.

Graphical overview of the obtained results are shown in FIGS. 4A and 4B. Cell population analysis by this objective tool reveals an increased NCR and OHD in the dysplastic cells. A correlation can be observed between the OHD and the diagnosis. This correlation allows the application of an automatic scoring algorithm in a smear in a liquid cell sample without the need for additional expensive preparation to make a cytological diagnosis. Complementary tests such as for HPV analysis are possible.

While there have been described herein what are to be considered exemplary and preferred embodiments of the present invention, other modifications of the invention will become apparent to those skilled in the art from the teachings herein.

What is claimed is:

1. A method for classifying cells in a cell sample comprising the following steps:
   providing a cell sample;
   obtaining holographic information from said cell sample by digital holographic microscopy (DHM);
   deriving at least one cellular parameter from said holographic information, and;
   classifying said cells of cell sample based on the at least one cellular parameter derived from holographic information of the cell sample obtained from the DHM;
   whereby in that said classification occurs based on said cellular parameters;
   characterized in that the at least one cellular parameter comprises a characteristic of nucleoli of the cells.

2. A method according to claim 1, said at least one cellular parameter comprising optical height of nucleoli of the cells.

3. A method according to claim 2, said at least one cellular parameter further comprising any ratio of the optical height of the nucleoli.

4. A method according to claim 1, characterized in that the cell sample is a liquid cell sample.

5. A method according to claim 4, wherein the cells are held in suspension in the liquid cell sample during the obtaining of the holographic information.

6. A method according to claim 1, characterized in that said at least one cellular parameter derived from obtained holographic information further comprises the optical nuclear height.

7. A method according to claim 1, characterized in that said at least one cellular parameter derived from obtained holographic information further comprises cell nucleus diameter, chromatin texture, cell size, cell form and cell morphology.

8. A method according to claim 1, characterized in that the classification occurs by appointing a Scoring Factor to said cells of the cell sample, based on said cellular parameters.

9. A method according to claim 1, comprising a step of detecting cancerous cells in the cell sample based on said cellular parameters.

10. A method according to claim 1, characterized in that classifying said cells of the cell sample is based upon comparison of said at least one cellular parameter and a threshold database.

11. A method according to claim 1, further comprising the step of performing an extra analysis, whereby the extra analysis comprises screening the cell sample for presence of topoisomerase 2 alpha.

12. A method according to claim 1, further comprising the step of performing an extra analysis, whereby the extra analysis comprises screening the cell sample for presence of one or more HPV genotypes and/or HPV viral proteins and/or one or more of the following list: p16 (INK4a), Ki67, topoisomerase 2 alpha, MCM2;
   said one or more HPV genotypes comprising one or more of the following list: HPV genotype 6, HPV genotype 11, HPV genotype 16, HPV genotype 18, HPV genotype 31, HPV genotype 40, HPV genotype 58, HPV genotype 58, HPV genotype c*31, HPV genotype 33, HPV genotype 54, HPV genotype c*33, HPV genotype 35, HPV genotype 39, HPV genotype 40, HPV genotype 42, HPV genotype 43, HPV genotype 44, HPV genotype 45, HPV genotype 51, HPV genotype 52, HPV genotype 53, HPV genotype 56, HPV genotype 74, HPV genotype c*56, HPV genotype 58, HPV genotype c*58, HPV genotype 59, HPV genotype 66, HPV genotype 68, HPV genotype 70, HPV c*68;
   said HPV viral proteins comprising one or more of the following list: HPV viral proteins E1-E7, L1-L2.

13. A method according to claim 1, further comprising the step of identifying the cellular type of said cells in the sample, prior to said classifying cells.

14. A method according to claim 1, characterized in that said cell sample is a cervical sample.

15. A system for the classification of cells in a cell sample comprising
   a digital holographic microscope (DHM) comprising illumination means, an interferometer and a digital recording device connected to a server;
   at least one exchangeable sample vial or sample carrier comprising a cell sample; and
   a computer or printer capable of providing a digital report related to said cell sample, wherein the digital report related to said cell sample comprises classification of said cells of the cell sample, wherein the classification of said cells is based on at least one cellular parameter derived from holographic information of the cell sample obtained from the DHM, and wherein the at least one cellular parameter comprises a characteristic of nucleoli of the cells.

16. A system according to claim 15, whereby said server is provided with algorithms for the comparison of said cellular parameters with a threshold database.

17. A system according to any of the claim 15, whereby said exchangeable sample vial or sample carrier comprises identifying indicia.

18. A system according to claim 17, whereby said identifying indicia comprise an RFID.

19. A system according to claim 15, whereby the cell sample is a liquid cell sample.

20. A system according to claim 19, whereby the cells are held in suspension in the liquid cell sample.

21. A method for updating and/or improving a database comprising thresholds linked to holographic information, comprising the steps of:

obtaining holographic information linked to a sample characterized in that said holographic information is obtained using digital holographic microscopy (DHM);

deriving at least one parameter from said holographic information;

comparing said parameter to said thresholds stored in database;

classifying objects in the sample based on said comparison of said parameter, wherein said parameter is derived from holographic information of the sample obtained using DHM, and said thresholds;

reporting said classification of said objects to a practitioner;

obtaining feedback of said practitioner with regards to said classification; and updating said database on the basis of said feedback;

characterized in that said at least one parameter comprises optical height of nucleoli of cells in the sample.

22. A method according to claim 21, storing identification information linked to said sample.

23. A method according to claim 22, whereby said sample is a cell sample, more preferably a liquid cell sample.

24. A database of objects comprising:

holographic information obtained from a sample comprising said objects using a digital holographic microscope and/or parameters derived thereof;

thresholds and queries related to said thresholds for the analysis of said holographic information and/or parameters;

classifications of the objects derived from said holographic information obtained from the sample using the digital holographic microscope and/or parameters derived thereof;

image identification;

identification information;

characterized in that said thresholds and queries of database are updated based upon receiving feedback information from a third party, and whereby the holographic information and/or parameters comprises a characteristic of nucleoli of cells in the sample.

25. A database according to claim 24, whereby said characteristic comprises optical height of the nucleoli of the cells in the sample.

26. A database according to claim 24, whereby said sample is a cell sample, more preferably a liquid cell sample.

* * * * *

UNITED STATES PATENT AND TRADEMARK OFFICE
CERTIFICATE OF CORRECTION

| | |
|---|---|
| PATENT NO. | : 10,025,271 B2 |
| APPLICATION NO. | : 15/497796 |
| DATED | : July 17, 2018 |
| INVENTOR(S) | : Philip Mathuis |

It is certified that error appears in the above-identified patent and that said Letters Patent is hereby corrected as shown below:

On the Title Page

Page 3 in Column 2, Line 32, under Other Publications, please change "10.1039/c01c00212g." to --10.1039/cO1c00212g.--.

In the Drawings

On Sheet 1 of 4, Line 3 (box 1), please change "Superfial" to --Superficial--.

On Sheet 1 of 4, Line 1 (box 2), please change "Meduim" to --Medium--.

On Sheet 1 of 4, Line 4 (box 4), please change "Polynucear" to --Polynuclear--.

In the Specification

In Column 4, Line 45, please change "HPV genotype 58, HPV genotype 58," to --HPV genotype 58,--.

In Column 4, Line 53, after "HPV" please insert --genotype--.

In Column 14, Line 51, please change "then" to --than--.

In Column 17, Line 17, please change "and or" to --and/or--.

In Column 19, Line 51, please change "database)" to --database).--.

In Column 20, Line 38, please change "Abott®" to --Abbott®--.

Signed and Sealed this
Twenty-sixth Day of March, 2019

Andrei Iancu
*Director of the United States Patent and Trademark Office*

CERTIFICATE OF CORRECTION (continued)
U.S. Pat. No. 10,025,271 B2

In the Claims

In Column 22, Lines 19-20, Claim 12 please change "HPV genotype 58, HPV genotype 58," to --HPV genotype 58,--.

In Column 22, Line 28, Claim 12 after "HPV" please insert --genotype--.

In Column 22, Line 56, Claim 17 after "to" please delete "any of the".